(12) United States Patent
Thuemen

(10) Patent No.: US 11,550,141 B2
(45) Date of Patent: Jan. 10, 2023

(54) VIDEO ENDOSCOPE AND BRAKE ELEMENT

(71) Applicant: OLYMPUS WINTER & IBE GMBH, Hamburg (DE)

(72) Inventor: Alrun Thuemen, Hamburg (DE)

(73) Assignee: OLYMPUS WINTER & IBE GMBH, Hamburg (DE)

( * ) Notice: Subject to any disclaimer, the term of this patent is extended or adjusted under 35 U.S.C. 154(b) by 0 days.

(21) Appl. No.: 17/291,670

(22) PCT Filed: Oct. 21, 2019

(86) PCT No.: PCT/EP2019/078500
§ 371 (c)(1),
(2) Date: May 6, 2021

(87) PCT Pub. No.: WO2020/099067
PCT Pub. Date: May 22, 2020

(65) Prior Publication Data
US 2022/0003982 A1    Jan. 6, 2022

(30) Foreign Application Priority Data

Nov. 13, 2018 (DE) .......................... 102018128306.7

(51) Int. Cl.
*G02B 23/24* (2006.01)
*H04N 5/232* (2006.01)
*H04N 5/225* (2006.01)

(52) U.S. Cl.
CPC ....... *G02B 23/2484* (2013.01); *G02B 23/243* (2013.01); *H04N 5/23296* (2013.01); *H04N 2005/2255* (2013.01)

(58) Field of Classification Search
CPC .. B67D 1/1234; B67D 1/0888; B67D 1/1477; B67D 2210/00091; B67D 1/1405;
(Continued)

(56) References Cited

U.S. PATENT DOCUMENTS 4,907,788 A    3/1990  Balsells
5,717,807 A *  2/1998  Theroux ................. G02B 6/032
                                                            606/15
(Continued)

FOREIGN PATENT DOCUMENTS

DE    102011078968 A1    1/2013
DE    102013213232 A1    1/2015
EP         3376061 A1    9/2018

OTHER PUBLICATIONS

International Preliminary Report on Patentability dated May 18, 2021 received in PCT/EP2019/078500.
(Continued)

*Primary Examiner* — Gims S Philippe
(74) *Attorney, Agent, or Firm* — Scully, Scott, Murphy & Presser, P.C.

(57) ABSTRACT

A video endoscope with lateral viewing direction including a shaft having proximal and distal ends, an objective lens in the distal end, an image sensor, and a main body at the proximal end. Where a first grip rotationally fixed relative to the shaft and the main body to rotate the shaft and the main body to change the viewing direction of the objective lens. A second grip is disposed on the main body to be rotatable relative to the shaft and the main body to maintain a horizontal position of the image sensor when the viewing direction is changed. An annular seal is disposed between the second grip and the main body and/or the first grip. The seal includes a circumferentially wound coil spring having windings oriented such that a surface vector of a surface spanned by a single winding points substantially in a circumferential direction of the seal.

17 Claims, 4 Drawing Sheets

(58) Field of Classification Search
CPC .. H04N 5/2253; H04N 5/2254; H04N 5/2256; H04N 7/183; H04N 7/18
USPC .......................................................... 348/76
See application file for complete search history.

(56) References Cited

U.S. PATENT DOCUMENTS

| | | | |
|---|---|---|---|
| 5,797,836 | A | 8/1998 | Lucey et al. |
| 5,905,923 | A | 5/1999 | Chitsaz et al. |
| 5,935,126 | A | 8/1999 | Riza |
| 10,365,470 | B2 | 7/2019 | Wieters et al. |
| 2005/0054951 | A1* | 3/2005 | Parins .................. A61M 25/09 600/585 |
| 2007/0112254 | A1 | 5/2007 | Weigel et al. |
| 2013/0149029 | A1 | 6/2013 | Changsrivong et al. |
| 2013/0158410 | A1* | 6/2013 | Ohgishi .................. A61B 8/12 600/462 |
| 2013/0245376 | A1* | 9/2013 | Oku .................... A61B 1/0011 600/129 |
| 2014/0051928 | A1* | 2/2014 | Fouts .................... A61B 1/018 600/114 |
| 2014/0128679 | A1 | 5/2014 | Wieters et al. |
| 2016/0124211 | A1 | 5/2016 | Wieters et al. |
| 2017/0340399 | A1* | 11/2017 | Ogawa .................. A61B 34/37 |

OTHER PUBLICATIONS

International Search Report dated Feb. 3, 2020 issued in PCT/EP2019/078500.
German Office Action dated Aug. 29, 2019 issued in DE 102018128306.7.
BAL SEAL Engineering INC: Solutions for rotary applications, Product catalogue of 2010—company publication URL: www.balseal.com, Archived in webarchive.org on Sep. 21, 2017 [retrieved from webarchive.org on Aug. 27, 2019], cited in German OA.
Wikipedia, the free encyclopedia: "Garter spring", Internet document from Oct. 6, 2015, Archived in webarchive.org on Oct. 21, 2016 [retrieved on Aug. 27, 2019], cited in German OA.

* cited by examiner

VIDEO ENDOSCOPE AND BRAKE ELEMENT

CROSS-REFERENCE TO RELATED APPLICATION

The present application is based upon and claims the benefit of priority from PCT/EP2019/078500 filed on Oct. 21, 2019, which claims priority to DE 10 2018 128 306.7 filed on Nov. 13, 2018, the entire contents of each of which is incorporated herein by reference.

BACKGROUND

Field

The present disclosure relates to a video endoscope and more particularly to a video endoscope with lateral viewing direction, comprising an elongated shaft having a proximal end and a distal end, an objective lens disposed in the portion of the distal end of the shaft, an electronic image converter disposed proximate to the objective lens and a main body disposed at the proximal end of the shaft, wherein a first grip element is disposed on the main body, the first grip element being rotationally fixed with respect to the shaft and the main body and serving to rotate the shaft and the main body about a longitudinal axis of the shaft in order to change the viewing direction of the video endoscope; a second grip element is disposed on the main body, the second grip element being rotatable relative to the shaft and the main body about a longitudinal axis of the shaft and serving to maintain a horizontal position of the electronic image converter when the viewing direction of the video endoscope is changed by rotating the first grip element; and between the second grip element and the main body, at least one annular elastic brake element is disposed.

Furthermore, the present disclosure relates to an annular brake element.

Prior Art

Video endoscopes are used in medicine since some time to optically examine and, if necessary, treat areas of a human or animal patient that are difficult to access. For this purpose, video endoscopes usually comprise an elongated shaft that is inserted through a natural or surgically created body orifice into the area of interest. A main body is located at the proximal end of the shaft, where the video endoscope can be held and controlled. An objective lens is disposed at the distal end of the shaft, which projects an image of the region of interest onto an electronic image converter (such as an image sensor) disposed proximate to the objective lens. The image converter generates an electronic video signal which is transmitted via signal lines extending in the shaft or wirelessly to the main body and from there to a control unit. From the control unit, the video signal may be routed to a monitor and/or a video recording device.

In order to enlarge the observable area, video endoscopes often have a lateral viewing direction, i.e. a viewing direction that deviates from the longitudinal axis of the shaft by a certain angle. By rotating the shaft, this viewing direction may be rotated.

In order to maintain a horizontal position of the video image when the shaft is rotated, the electronic image converter must be kept constant in its rotational position. For this purpose, known video endoscopes comprise two grip elements on the main body. A first grip element is non-rotatably connected to the shaft and the main body, so that the shaft and thus the viewing direction of the video endoscope may be rotated by rotating the first grip element. For example, the first grip element may include a rotation ring disposed at the distal end of the main body. A second grip element is rotatable relative to the first grip element and the main body, and is coupled to the image converter such that the rotational orientation of the image converter always corresponds to the rotational orientation of the second grip element.

Now, in order to change the viewing direction of the video endoscope, the user may rotate the first grip element with one hand while holding the second grip element with the second hand. By doing so, the horizontal position of the video image remains stable.

To ensure a comfortable and safe operation of the video endoscope, a torque to be applied to rotate the viewing direction is adjusted by means of an annular elastic brake element disposed between the second grip element and the main body and/or the first grip element.

Gaps inevitably occur between parts that are rotatable against each other, such as the second grip element and the main body and/or the first grip element, into which moisture and soiling may enter during the use of a video endoscope. These gaps are difficult to clean during reconditioning of the video endoscope. The installed ring-shaped elastic brake elements may also achieve a certain sealing effect in order to prevent moisture or soiling from entering.

Corresponding video endoscopes are marketed, for example, by the applicant under the name "ENDOEYE".

In the prior art, sealing rings made of an elastomer such as rubber or silicone are usually used as annular elastic brake elements. Such sealing rings have sufficient resistance to mechanical, thermal and chemical impacts, which affect the sealing rings mainly during the reconditioning of video endoscopes.

However, even though the sealing capability of known elastomer seals remains intact over many reprocessing cycles, changes occur regarding the properties of the sealing rings. In particular, it has been observed that over time, the sliding properties of the sealing rings change, making it more difficult to rotate the second grip element relative to the main body. This is troublesome when using the video endoscope.

SUMMARY

It is therefore an object to provide a video endoscope and an annular brake element which are improved with respect to the described problem.

According to an embodiment, such object can be achieved by a video endoscope with a lateral viewing direction, comprising an elongated shaft having a proximal end and a distal end, an objective lens disposed in the portion of the distal end of the shaft, an electronic image converter (i.e., an image sensor) disposed proximate to the objective lens and a main body disposed at the proximal end of the shaft, wherein a first grip element is disposed on the main body, the first grip element being rotationally fixed with respect to the shaft and the main body and serving to rotate the shaft and the main body about a longitudinal axis of the shaft in order to change the viewing direction of the video endoscope; a second grip element is disposed on the main body, the second grip element being rotatable relative to the shaft and the main body about a longitudinal axis of the shaft and serving to maintain a horizontal position of the electronic image converter when the viewing direction of the video endoscope is changed by rotating the first grip element; and between the second grip element and the main body and/or the first grip element, at least one annular elastic brake element is disposed, wherein the at least one annular elastic brake element comprises a circumferentially wound coil spring, the windings of which are oriented such that a surface vector of a surface spanned by a single winding points substantially in a circumferential direction of the brake element.

With such a configuration, both the sliding properties and the sealing properties of the coil spring are significantly less affected by mechanical, thermal and/or chemical influences than the corresponding properties of an elastomer seal. At the same time, it has been surprisingly found that the gaps that inevitably occur in a circumferentially wound coil spring do not significantly impair the sealing effect of the coil spring against the ingress of soiling or moisture.

In a further embodiment of a video endoscope, the coil spring may be disposed between a first contact surface and a second contact surface in such a way that the windings of the coil spring slide along the first contact surface and/or the second contact surface during a rotation of the second grip element relative to the main body. As a result, the high long-term stability of the coil spring directly benefits the sliding behavior of the video endoscope.

The coil spring may be made of conductive material, such as spring steel, while the first and/or second contact surface may be made of non-conductive material, such as plastic. Such a combination of materials offers, on the one hand, particularly pleasant sliding properties and, on the other hand, provides electrical insulation of the contact surfaces from one another, similar to a classic elastomer seal.

In a further embodiment, a labyrinth or gap seal may be disposed in front of or behind the at least one annular brake element. Such additional brake elements may further improve the sealing effect without affecting the sliding properties of the brake element.

In an embodiment of a video endoscope, between the second grip element and the main body and/or the first grip element, two elastic brake elements may be disposed, each of which comprises a coil spring wound in the circumferential direction.

Therein, a first elastic brake element may be disposed in a portion of a proximal end of the main body, and a second elastic brake element may be disposed in a portion of a distal end of the main body. By this means, the second grip element is guided on the main body in a particularly firm manner. In addition, a cavity between the main body and the second grip element, which extends over the length of the main body, may thus be sealed on both sides.

In another embodiment of a video endoscope, the coil spring may have a non-circular coil cross-section. In this context, a largest diameter of the coil cross-section of the coil spring may be aligned in the longitudinal direction of the shaft. A smallest diameter of the coil cross-section of the coil spring may be aligned perpendicular to the longitudinal axis of the shaft.

Such a design of the coil spring has various advantages. For example, the non-circular shape prevents the coil spring from rolling in the longitudinal direction of the shaft during assembly, in which case the spring may be unevenly twisted, which in turn would result in an uneven braking and/or sealing effect. At the same time, the smaller radii of curvature on the inside and outside of the coil spring reduce the surface pressure on the contact surfaces.

In a further embodiment of a video endoscope, the at least one brake element is disposed in a radial gap, the radial height of the gap being at least 10%, such as at least 25%, smaller than the smallest diameter of the coil cross-section of the coil spring. The radial height of the gap can be at least 50% of the smallest diameter of the coil cross-section of the coil spring.

The lower height of the gap compresses the coil spring perpendicular to the longitudinal axis of the shaft, tilting the individual coils of the coil spring. The tilt angle is about 25° when the height of the gap is 10% smaller than the smallest diameter of the coil cross-section of the coil spring, and about 40° when the height of the gap is 25% smaller than the smallest diameter of the coil cross-section of the coil spring.

In a further embodiment of a video endoscope, the at least one brake element is arranged in a radial gap, the radial height of the gap being less than 20%, such as less than 15%, or less than 10%, of a mean radius of the gap. By means of a corresponding dimensioning of the gap, it is ensured that the gaps between the individual windings of the coil spring do not become as wide as to impair the sealing effect. The radial height of the gap can be at least 1% of the mean radius of the gap.

The coil spring may be wound from a wire of substantially circular cross-section.

Such object can be further achieved by a brake element of a video endoscope according to the above embodiments. In this regard, with respect to embodiments as well as the effects and advantages achievable hereby, reference is expressly made to what has been said above.

BRIEF DESCRIPTION OF THE DRAWINGS

The embodiments are described in more detail below with reference to a number of exemplary drawings. In this context, the illustrated embodiments serve merely to provide a better understanding of the invention, without limiting it to the embodiments, in which.

DETAILED DESCRIPTION

Figure 1:
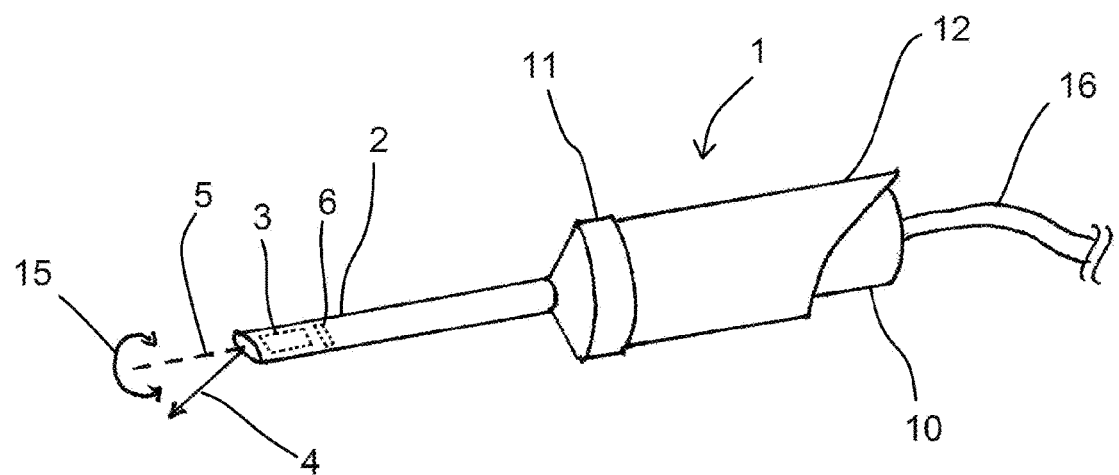
FIG. 1 illustrates a video endoscope.

FIG. 1 shows a video endoscope 1 with an elongated shaft 2, in the distal end of which an objective lens 3 is disposed. The objective lens has a lateral viewing direction, i.e., a viewing direction of the objective lens 3 indicated by the arrow 4 deviates from a longitudinal axis 5 of the video endoscope 1.

Furthermore, the video endoscope 1 has a main body 10 on which a first grip element 11 and a second grip element 12 are disposed.

The first grip element 11 is configured as a rotary wheel at the distal end of the main body. By means of the first grip element 11, the shaft 2, the objective lens 3, and the main body 10 may be rotated about the longitudinal axis 5 of the endoscope, so that the viewing direction of the video endoscope also rotates about the longitudinal axis 5 of the video endoscope. This is indicated by the double arrow 15.

An electronic image converter (i.e., an image sensor) 6 is disposed in the shaft 2 proximal to the objective lens 3, for example a CCD chip or a CMOS chip. Of course, a plurality of image converters may also be provided to image different color spaces or partial images of a stereo optical system. The electronic image converter converts the image projected by the objective lens 3 into electrical signals, which are transmitted through the shaft 2 into the main body 10 and from there via a cable 16 to an external processing device, which is not shown. The processing device, a controller, such as a CPU or computer, may process the electrical signals, for example, for display on a monitor or for storage in a memory element.

In order to maintain the horizontal position of the video image when the viewing direction of the video endoscope 1 is being rotated, the image converter is rotatably arranged in the shaft 2, and is rotationally coupled to the second grip element 12. For this purpose, a magnetic coupling acting through the shaft or through the wall of the main body 10 is provided. The structure of this magnetic coupling is known as such and need not be explained in detail here.

The second grip element 12 is rotatably disposed with respect to the first rotary body 11 and the main body 10. When the viewing direction of the video endoscope is now rotated by turning the first grip element 11, the second grip element 12 may simultaneously be held in place, whereby the orientation of the electronic image converter also remains constant.

Figure 2:
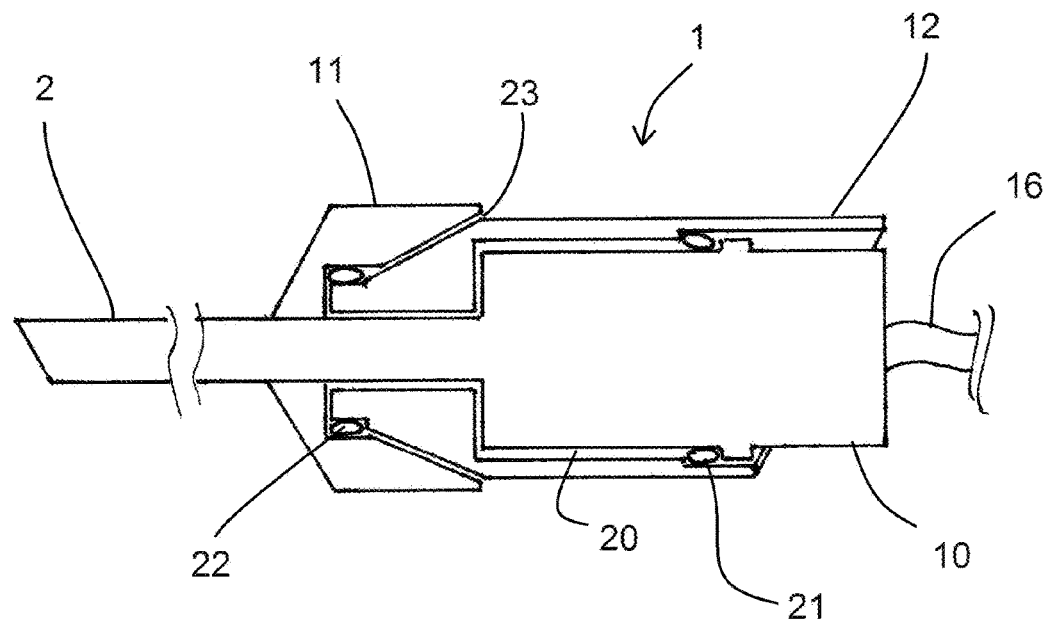
FIG. 2 illustrates a video endoscope in a sectional view.

In FIG. 2, the video endoscope 1 is shown in a simplified sectional view, with the interior of the shaft 2 and the main body 10 not shown for reasons of clarity.

It can be seen that the first grip element 11 is non-rotatably connected to the shaft 2 in the vicinity of the transition from the shaft 2 into the main body 10. The second grip element 12 extends from the proximal end of the main body 10 to the distal end thereof, and extends there between the main body 10 and the first grip element 11.

In order to adjust a torque required to rotate the viewing direction of the video endoscope 1, annular elastic brake elements 21, 22 (i.e., seals) are disposed between the main body 10 and the second grip element 12, and between the first grip element 11 and the second grip element 12, as will be explained in detail below.

A cavity 20 is formed between the main body 10, the first grip element 11, and the second grip element 12, into which moisture and soiling may enter during use of the video endoscope 1, which may only be removed with difficulty.

The brake elements 21, 22 additionally act as seals to prevent moisture and soiling from entering the cavity 20. In addition, a gap 23 between the first grip element 11 and the second grip element 12 is made particularly narrow so that it acts as an additional gap seal.

Figure 3:
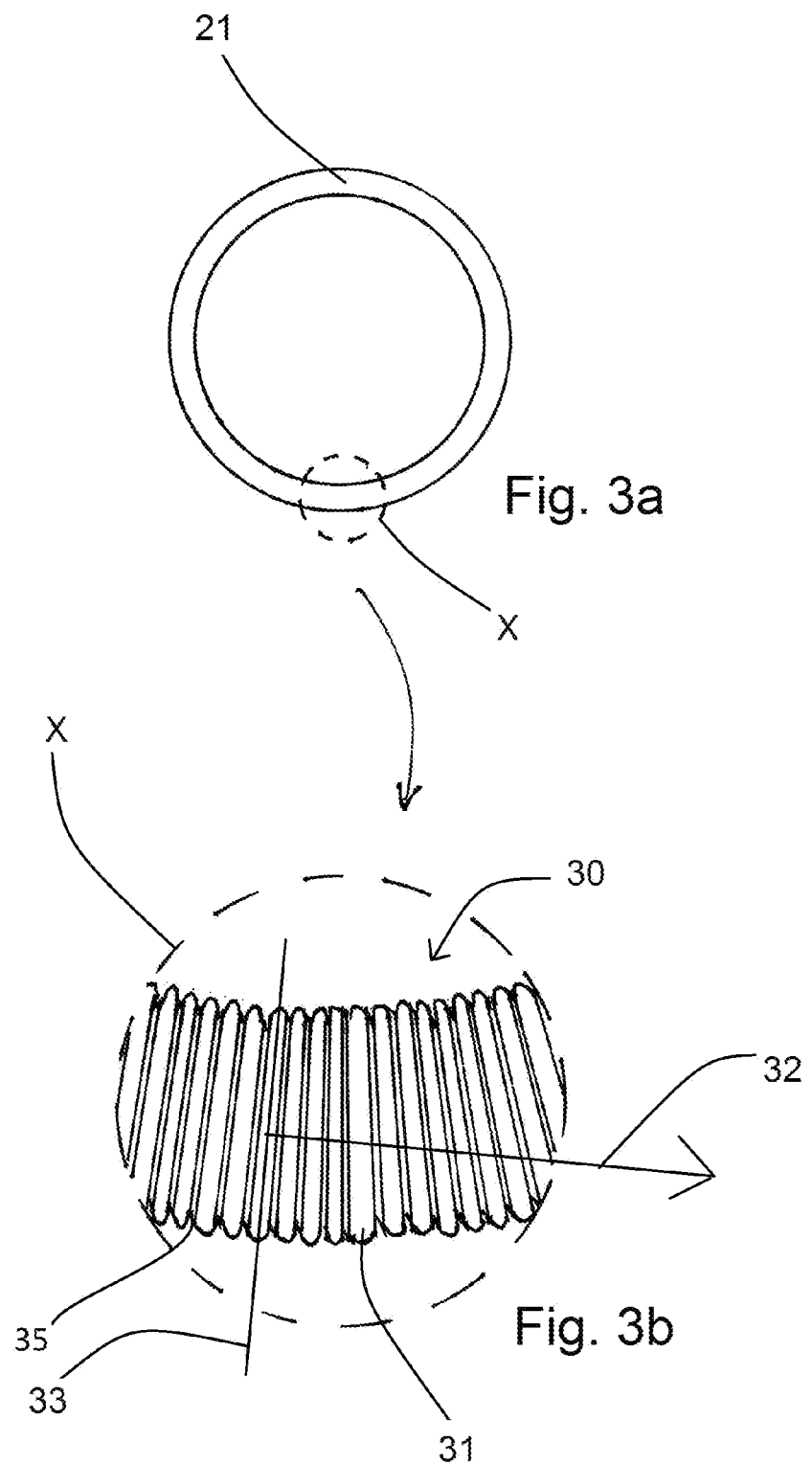
FIG. 3a illustrates an elastic brake element.
FIG. 3b illustrates a sectional enlargement of FIG. 3a,
FIG. 4 illustrates a sectional view of an elastic brake element.

In FIG. 3a, the elastic brake element 21 is shown in an unloaded state in a front view, and FIG. 3b shows an enlarged view of a section X of FIG. 3a.

It can be seen that the brake element 21 consists of a coil spring 30. The individual windings 31 of the coil spring 30 are oriented in such a way that a surface vector 32 of a surface 33 spanned by an individual winding 31 points substantially in a circumferential direction of the brake element 21.

The coil spring 30 is wound from a metal wire having a substantially circular cross-section. For example, stainless steel is suitable as a material for the coil spring 30.

To produce the annular brake element 21, the coil spring may first be wound along the circumferential length of the brake element as a straight coil spring and then elastically bent to form a ring. The ends of the coil spring may then be joined together, for example welded, to form an endless annular coil spring.

In the outer portion of the brake element 21, the annular shape inevitably results in small gaps 35 between the windings 31 of the coil spring 30. To prevent these gaps from becoming large enough to impair the sealing effect of the brake element 21, the radial height of a gap into which the brake element 21 is inserted is significantly smaller than the mean radius of the gap. The height of the gap can be less than 20%, such as less than 15%, and less than 10% of the mean radius of the gap.

Figure 4:
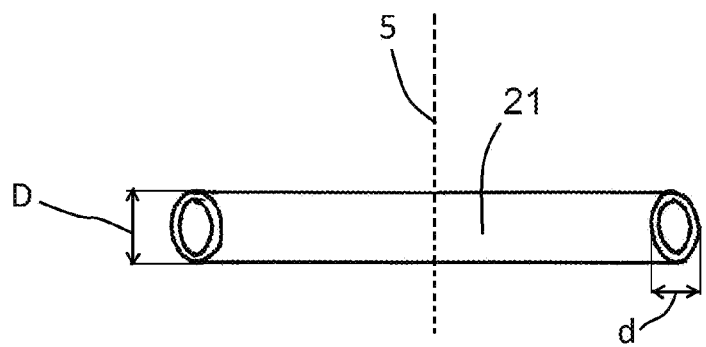

In FIG. 4, the elastic brake element 21 is shown in cross-section. It can be seen that the coil cross-section of the brake element 21 is non-circular, being approximately elliptical. Herein, a largest diameter D of the coil cross-section is aligned in the direction of the longitudinal axis 5 of the shaft 2, while a smallest diameter d of the coil cross-section is aligned perpendicular to the longitudinal axis 5 of the shaft 2.

The non-circular coil cross-section of the brake element 21 prevents the brake element 21 from rolling along the contact surfaces when the video endoscope 1 is assembled, for example when the second grip element 12 is slid axially over the main body 10. In this case, the coil spring 30 could twist unevenly, so that the braking and/or sealing effect of the brake element 21 would be impaired.

Figures 5A, 5B, 5C:
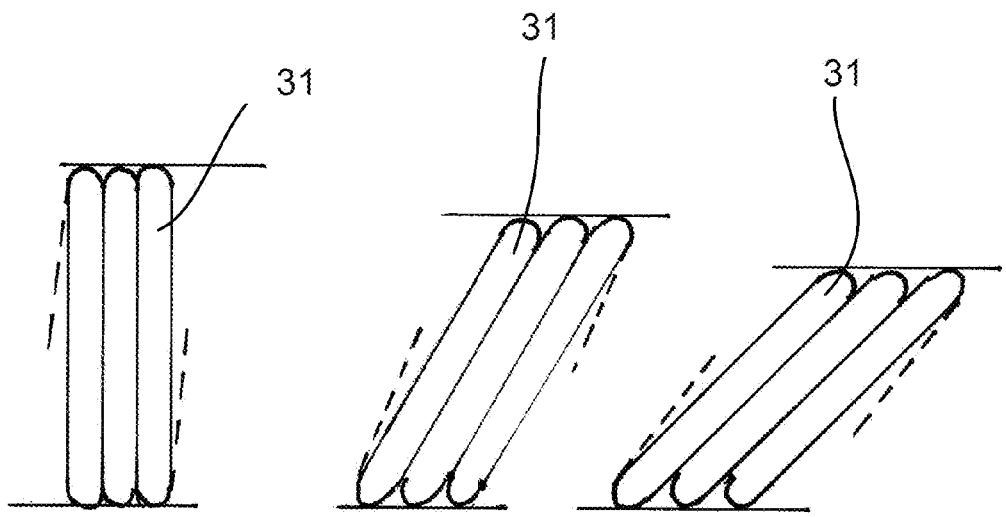
FIG. 5a illustrates a section of a brake element in unloaded condition.
FIGS. 5b and 5c illustrate a section of a brake element in a loaded condition.

FIGS. 5a to 5c show the influence of the height of a gap in which the elastic brake elements 21, 22 are inserted on the structure of the coil spring 30.

FIG. 5a shows the position of the windings 31 of the coil spring in a relaxed state, here the windings 31 run approximately perpendicular to the circumferential direction of the brake element.

FIG. 5b shows the situation when the height of the gap is about 10% smaller than the winding diameter of the coil spring 30. It can be seen that the windings 31 move elastically to one side, in FIG. 5b by about 25°. In the process, the coil spring 30 builds up a restoring force which ensures a uniform and sealing contact of the coil spring 30 with the contact surfaces.

The restoring force of the coil spring 30 essentially determines the friction between the brake element 30 and the respective contact surfaces and thus the force to be applied by the user when rotating the viewing angle of the video endoscope 1. Since the restoring force is hardly affected by exposure to chemical or thermal influences, the friction remains constant over a long period of time and over many reconditioning cycles. The exact restoring force of the coil spring 30, which is required for a comfortable handling of the video endoscope 1, strongly depends on the dimensions of the video endoscope 1 and the materials in use. It can be found for a specific video endoscope 1 without difficulty by simple experiments.

When the second grip element 12 is rotated relative to the main body 10 of the video endoscope 1, the windings 31 of the coil spring 30 slide along either the inner contact surface or the outer contact surface. Steel for the coil spring and plastic, e.g., polytetrafluoroethylene (PTFE) or polyethylene (PE), for the contact surface have proven to be a particularly advantageous material combination in this case. A non-conductive contact surface offers the additional advantage that the sections of the video endoscope (1) that are rotatable against each other are electrically insulated from each other, which corresponds to the conditions when using classic elastomer seals.

FIG. 5c shows a situation in which the height of the gap is about 25% smaller than the winding diameter of the coil spring 30. Here, the windings 31 are inclined by an angle of about 40°.

Figure 6:
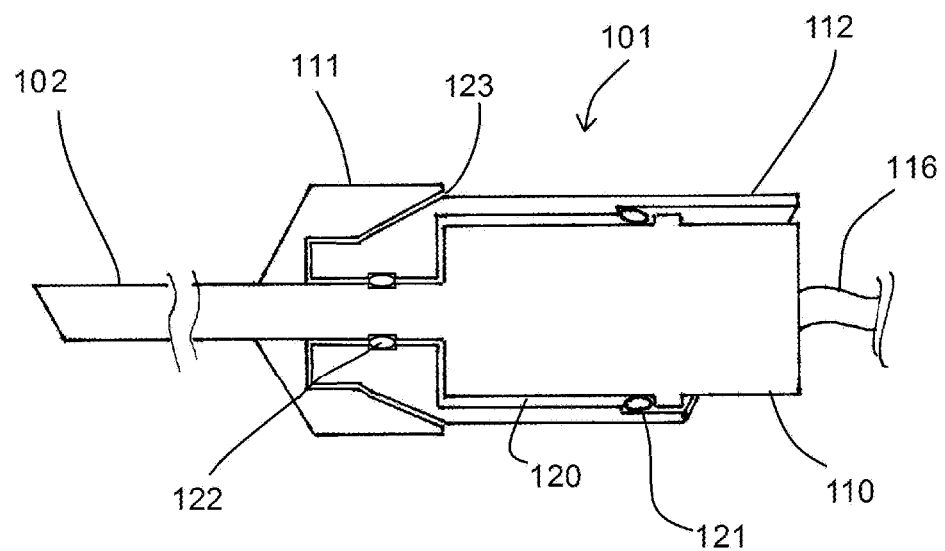
FIG. 6 illustrates another video endoscope in a sectional view.

The configuration of the brake element 22 corresponds to the described configuration of the brake element 21. FIG. 6 shows an alternative configuration of a video endoscope 101. This corresponds essentially to the configuration of the video endoscope 1 shown in FIG. 2, wherein corresponding elements are provided with a reference sign increased by 100 and are not explained again in detail.

Unlike in the video endoscope 1, in the video endoscope 101, the second brake element 122 is not disposed between the first grip element 111 and the second grip element 112, but between the second grip element 112 and the main body 110 in the vicinity of the transition into the shaft 102.

As a further feature, the brake element 122 is disposed between an inner slot formed in the main body 110 and an outer slot formed in the second grip element 112. This makes it possible to achieve that, during assembly of the video endoscope 101, the brake element 122 virtually engages between the two slots and thus noticeably indicates the correct positioning. A corresponding embodiment may of course also be used for the first brake element 121.

While there has been shown and described what is considered to be preferred embodiments of the invention, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

The invention claimed is:

1. A video endoscope with a lateral viewing direction, the video endoscope comprising:
   an elongated shaft having a proximal end and a distal end,
   an objective lens disposed in a portion of the distal end of the shaft,
   an image sensor disposed proximally relative to the objective lens, and
   a main body disposed at the proximal end of the shaft, wherein
   a first grip disposed on the main body, the first grip being rotationally fixed with respect to the shaft and the main body, the first grip being configured rotate the shaft and the main body about a longitudinal axis of the shaft in order to change the viewing direction,
   a second grip disposed on the main body, the second grip being rotatable relative to the shaft and the main body about the longitudinal axis of the shaft, the second grip being configured to maintain a horizontal position of the image sensor when the viewing direction of the objective lens is changed by rotating the first grip, and
   at least one annular seal disposed between one or more of the second grip and the main body and the second grip and the first grip,
   the at least one annular seal comprises a circumferentially wound coil spring having windings, the winding being oriented such that a surface vector of a surface spanned by a single winding points substantially in a circumferential direction of the seal.

2. The video endoscope according to claim 1, wherein the coil spring is disposed between a first contact surface and a second contact surface in such a way that the windings of the coil spring slide along the one or more of the first contact surface and the second contact surface during a rotation of the second grip relative to the main body.

3. The video endoscope according to claim 2, wherein the coil spring is formed of a conductive material and one or more of the first and second contact surface is formed of a non-conductive material.

4. The video endoscope according to claim 3, wherein the conductive material is spring steel.

5. The video endoscope according to claim 3, wherein the non-conductive material is plastic.

6. The video endoscope according to one of claim 1, further comprising one of a labyrinth seal or gap seal is adjacent to the at least one annular seal.

7. The video endoscope according to claim 1, wherein the at least one annular seal comprises first and second annular seals disposed between the second grip and the main body and between the second grip and the first grip, respectively.

8. The video endoscope according to claim 7, wherein the first seal is disposed in a portion of a proximal end of the main body and the second annular seal is disposed in a portion of a distal end of the main body.

9. The video endoscope according to claim 1, wherein the coil spring has a non-circular coil cross-section.

10. The video endoscope according to claim 9, wherein a largest diameter of the coil cross-section of the coil spring is aligned in a longitudinal direction of the shaft.

11. The video endoscope according to claim 9, wherein a smallest diameter of the coil cross-section of the coil spring is aligned perpendicular to a longitudinal axis of the shaft.

12. The video endoscope according to claim 1, wherein the at least one seal is disposed in a radial gap, a radial height of the gap being at least 10% smaller than a smallest diameter of a coil cross-section of the coil spring.

13. The video endoscope according to claim 12, wherein the radial gap being at least 25% smaller than the smallest diameter of the coil cross-section of the coil spring.

14. The video endoscope according to claim 1, wherein the at least one seal is arranged in a radial gap, a radial height of the gap being less than 20% of a mean radius of the gap.

15. The video endoscope according to claim 14, wherein the radial height of the gap being less than less than 15% of a mean radius of the gap.

16. The video endoscope according to claim 15, wherein the radial height of the gap being less than less than 10% of a mean radius of the gap.

17. The video endoscope according to claim 1, wherein the coil spring is wound from a wire having a substantially circular cross-section.

* * * * *